United States Patent [19]

Seymour

[11] Patent Number: 5,110,213

[45] Date of Patent: May 5, 1992

[54] METHOD AND APPARATUS FOR MEASURING CONCENTRATION OF A MATERIAL IN A SAMPLE

[75] Inventor: Sydney K. Seymour, Clemmons, N.C.

[73] Assignee: R. J. Reynolds Tobacco Company, Winston-Salem, N.C.

[21] Appl. No.: 454,493

[22] Filed: Dec. 21, 1989

[51] Int. Cl.$^5$ .............................................. G01N 21/55
[52] U.S. Cl. .................................... 356/445; 356/243; 250/562; 131/908; 209/535
[58] Field of Search ................ 356/444, 445, 446, 430, 356/562, 243; 209/535, 536, 537; 422/67, 43, 73; 436/164, 805, 807; 250/562; 382/69; 131/274, 905, 906, 908, 342, 352, 358, 365

[56] References Cited

U.S. PATENT DOCUMENTS

| | | | |
|---|---|---|---|
| 3,744,496 | 7/1973 | McCarty et al. | 131/342 |
| 4,252,443 | 2/1981 | Lucas et al. | 356/430 |
| 4,411,518 | 10/1983 | Meserol et al. | 356/39 |
| 4,730,932 | 3/1988 | Iga et al. | 356/446 |
| 4,737,464 | 4/1988 | McConnell et al. | 436/43 |
| 4,906,099 | 3/1990 | Casasent | 356/394 |

OTHER PUBLICATIONS

Sony® Color Video Camera DXC-M2PH, Sony Corporation, 1985.
Technical Manual Volume 2 Image Processing Hardware, Kontron Bildanalyse, Image analysis Systems, Kontron Electronics, Jun. 1988.
SEM-IPS Manual, vol. II, IPS Measuring Program, Kontron Elektronik, Rel. 4.4, Oct. 1986.
MS-DOS User Reference Manual, Kontron Bildanalyse, Image Analysis Systems.
Intralux® 100/250 Module, Volpi AG, CH-8902 Urdorf/Zurich, Switzerland.

*Primary Examiner*—Vincent P. McGraw
*Assistant Examiner*—LaCharles P. Keesee
*Attorney, Agent, or Firm*—Grover M. Myers

[57] ABSTRACT

A method and apparatus for nondestructively, quickly and accurately measuring concentration of a material in a sample, for example carbon concentration in a carbon-containing sheet, by optically sensing a two-dimensional portion of the carbon-containing sheet and converting the sensed portion into a two-dimensional array of points, each having a digital value related to the sensed optical intensity at the point. Preferably, each point has a gray scale value of the sensed optical intensity at the point. An average digital gray scale value for the two-dimensional gray scale array of points is obtained and compared to the average digital gray scale value of a carbon-free sheet to obtain an optical density. The obtained optical density correlates highly with the carbon concentration, as measured by chemical concentration measurement techniques which are slow and destructive.

44 Claims, 3 Drawing Sheets

METHOD AND APPARATUS FOR MEASURING CONCENTRATION OF A MATERIAL IN A SAMPLE

FIELD OF THE INVENTION

This invention relates to measuring methods and apparatus and more particularly to a high-speed, accurate and nondestructive method and apparatus for measuring concentration of a material in a sample.

BACKGROUND OF THE INVENTION

In present day design and production systems, it is often necessary to measure the concentration of a material in a sample. For example, it is often necessary to measure concentration of particulate solid material in a sheet sample. In the tobacco products industry, in particular, it is important to measure concentration and consistency of carbon in a carbon-containing sheet. Such carbon-containing sheets typically comprise a mixture of tobacco and carbon, as described, for example in U.S. patent application Ser. No. 07/408,433, filed Sept. 15, 1989, entitled Smoking Article With Improved Means For Delivering Flavorants, which is assigned to the Assignee of the present invention. Crimped plugs of the carbon-containing sheet may be used as a flavor carrier by, for example, applying menthol and glycerine to the sheet. These carbon-containing sheets may also be used as filters for selectively absorbing particular compounds. In order to ensure high quality and uniformity of cigarettes it is desirable to measure the carbon concentration in the carbon-containing sheets to ensure that production tolerances are met.

Heretofore, a carbon tetrachloride ($CCl_4$) vapor absorption technique has been employed to measure carbon concentration in a carbon-containing sheet. In this technique, the sheet is exposed to $CCl_4$ vapors, and the $CCl_4$ absorption rate is monitored to monitor carbon concentration. Alternatively, a "wet digestion" technique has also been employed to measure carbon concentration. In a wet digestion process, a sample of the sheet is repeatedly soaked in solutions of HCl, $HCl+(NH_4)(C_2O_2)$, NaOH and $Cu(NH_3)_4(OH)_2$ to dissolve the tobacco, leaving the carbon behind as residue. The residual carbon may be weighed to obtain a carbon concentration. Other chemical processes for measuring carbon concentration are also known.

Unfortunately, vapor absorption, wet digestion or other chemical processes are time consuming, and cannot be employed in an "on line" monitoring system for performing quality control measurements on carbon-containing sheets during production. Moreover, wet digestion or other chemical techniques are "destructive" measuring techniques, in which at least a portion of the sheet needs to be destroyed in order to obtain the measurement. Nondestructive measuring techniques are preferred, to allow carbon concentration and distribution to be measured without destroying the sheet.

Photometric techniques have been employed in the measuring arts. For example, U.S. Pat. No. 4,252,443 to Lucas et al. discloses a blackening sensor which analyses a signal generated by the detection of scattered light reflected from a succession of small illuminated areas on the surface of a sheet, to provide an indication of the degree of blackening of the sheet. However, this system employs many analog circuits, such as filters, clippers, averaging circuits and thresholding circuits which are complicated, inaccurate and require frequent adjustment.

Another photometric technique is described in U.S. Pat. No. 4,737,464 to McConnell et al., which describes a solid state optical assay imaging apparatus including a 256 ×255 optical memory to store a digital image of a light modulated scanned object. A special optical memory is employed, having memory cells which decay due to the modulated light over a period of time as a function of the initial intensity of the light. The amount of time for 50% of the cells to change state is determined. This "half life" measurement time is then employed to obtain a measurement of optical concentration. Although this system uses digital circuits, the optical memory is expensive, and the need to rely on "half life" decay may create an inaccurate measurement.

SUMMARY OF THE INVENTION

According to the invention, concentration of a material in a sample may be accurately, rapidly and nondestructively measured by optically sensing a two-dimensional portion of the sample and converting the optically sensed portion into a two-dimensional digital image having a two-dimensional array of points, each having a digital value related to the sensed optical intensity at the point. Preferably, each point has a gray scale value of the sensed optical intensity at the point. According to the invention, an average digital value for the two-dimensional gray scale array of points is obtained. This digital value is converted into an optical density by comparing the obtained digital value to an average digital value for a material-free sample of the same type. The optical density may be computed by obtaining the logarithm of the ratio of the average gray scale value of the material-containing sample to the average gray scale value of a material-free sample.

The method and apparatus of the present invention may be employed to determine the concentration of any material contained in a sample, as long as the material blocks or reflects visible radiation incident on the sample, as a function of chemical composition. However, the invention is particularly advantageous for measuring carbon concentration in carbon-containing sheets for cigarette products, wherein wet digestion, vapor absorption or other chemical techniques have been the only concentration measurement techniques heretofore available.

According to a preferred embodiment of the invention, a two-dimensional digital image of a portion of the sample may be obtained using a video camera to provide a two-dimensional gray scale image. A general purpose data processor or a special purpose image processing system may be employed to compute the average gray scale value. The camera may be oriented to sense the light reflected from the sample or transmitted through the sample. The sample may be movably mounted relative to the camera to thereby obtain a large number of optical density measurements per sample, and thereby measure concentration consistency. Each sample may include a portion which is free of the material for reference calibration. Alternatively, a separate material-free reference may be measured before or after measuring the material-containing sample.

The method and apparatus of the present invention employs digital average gray scale techniques which may be easily implemented using readily available video cameras and a personal computer. It has been found that a measurement may be obtained in less than five seconds so that the system may be used for on-line measurements. Moreover, by comparing the optical density measurements obtained using the present invention to known wet digestion techniques, it has been found that a highly accurate measurement of carbon concentration is obtained by the present invention. In fact, a correlation of at least 98% with standard vapor absorption and wet digestion processes has been obtained. Accordingly, the optical density measuring technique of the present invention provides a high speed, accurate and nondestructive carbon concentration measuring technique.

DESCRIPTION OF THE PREFERRED EMBODIMENT

The present invention now will be described more fully hereinafter with reference to the accompanying drawings, in which a preferred embodiment of the invention is shown. This invention may, however, be embodied in many different forms and should not be construed as limited to the embodiment set forth herein; rather, this embodiment is provided so that this disclosure will be thorough and complete, and will fully convey the scope of the invention to those skilled in the art. Like numbers refer to like elements throughout.

Figure 1:
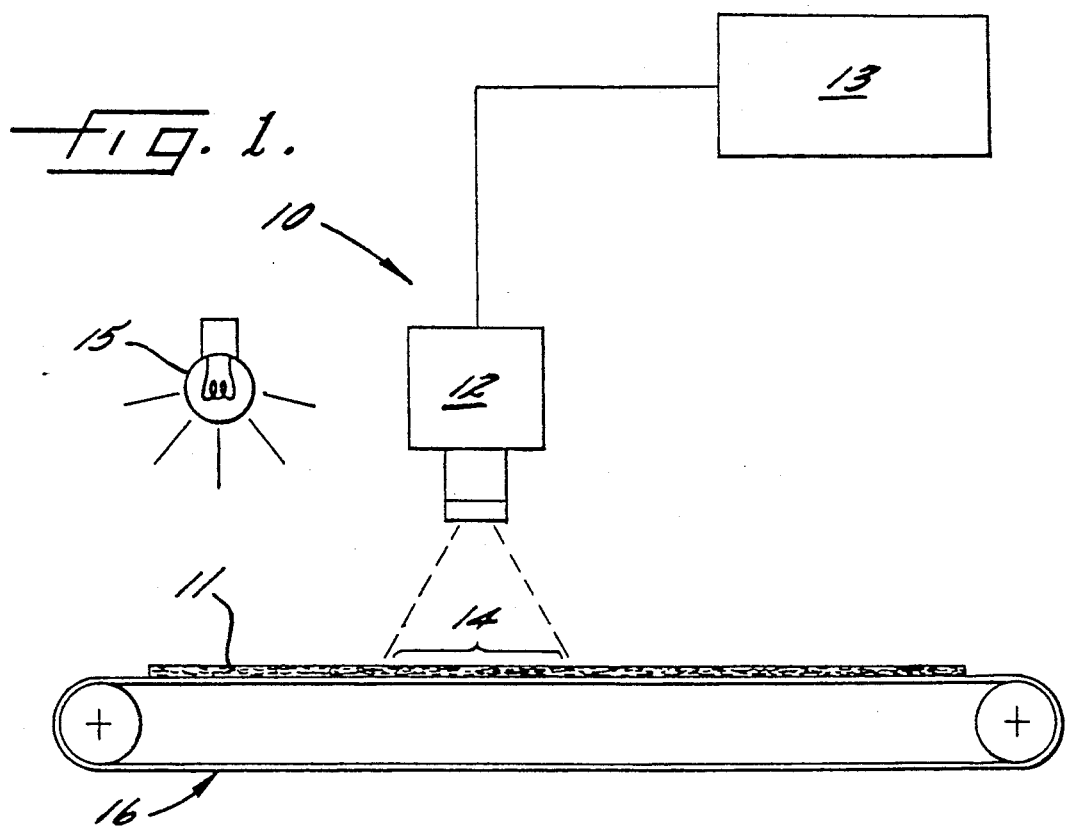
FIG. 1 is a schematic illustration of the method and apparatus for measuring carbon concentration in a carbon-containing sheet, according to the present invention.

Referring now to FIG. 1, the method and apparatus for measuring carbon concentration in a carbon-containing sheet according to the present invention will now be described However, it will be understood by those having skill in the art that concentrations of other materials in samples may be also measured, according to the present invention, as described below. Carbon concentration measuring system 10 includes a video camera 12 which may be a model DXC-M2PH video camera manufactured by Sony Corporation, Japan, for obtaining a two-dimensional image of the illuminated intensity of a target area 14 on a carbon-containing sample, shown as sheet 11 Target area 14 is illuminated by light source 15, which may for example be a ring light. In many applications, however, ordinary room fluorescent light may be sufficient. It will also be understood by those having skill in the art that the illumination frequency may be varied to obtain best results.

The Sony DXC-M2PH video camera described above is a high resolution video color camera, which may be operated in black-and-white mode to obtain a high resolution (625 lines) video signal. The camera may be focused on target area 14, for example 3"×3". The video camera 12 may be coupled to a general purpose data processor 13 or to a special purpose image processing system such as the IBAS Image Analysis System manufactured by Kontron Bildanalyse for digitizing the high resolution video signal to obtain 512×512×8 bits of gray scale intensity data, and for obtaining the average gray scale value as described below. It will also be understood by those having skill in the art that digitized gray scale data may be produced by the video camera 12 so that processor 13 need only compute the average gray scale value.

Carbon concentration measuring system 10 also includes a conveyor or other sample movement means 16 for effecting relative movement between camera 12 and sheet 11 It will be understood by those having skill in the art that conveyor 16 may provide continuous movement of sheet 11 past camera 12. Camera 12 may obtain instantaneous two-dimensional gray sale "snapshots" of target area 14. In order to obtain an instantaneous "snapshot", it may be desirable to pulse light source 15, under control of camera 12 or processor 13 to freeze the motion of the sheet. Alternatively, conveyor 16 may be driven in a discontinuous or stepwise motion, under control of processor 13, or under independent control. In this alternative camera 12 may be controlled to obtain the two dimensional snapshot when the sheet is stationary. Particular techniques for control and synchronization of processor 13, camera 12, light 15 and conveyor 16 are well known to those having skill in the art and will not be described further herein.

Figure 2:
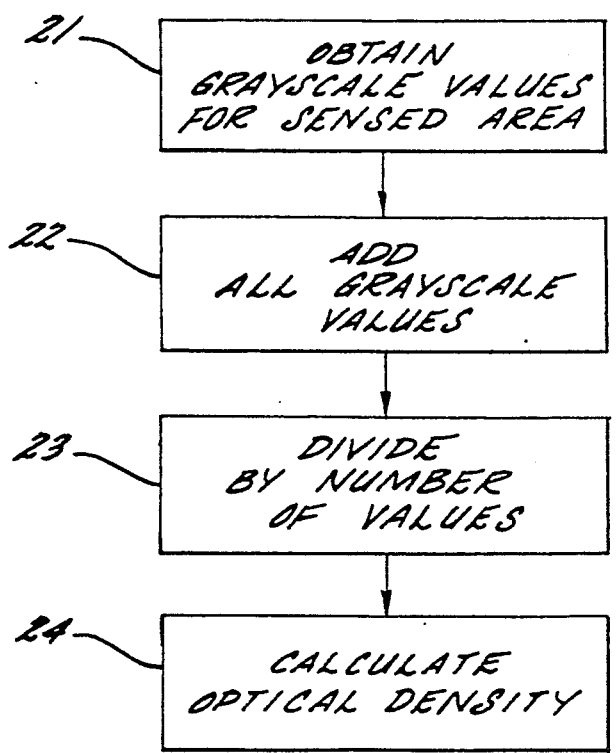
FIG. 2 schematically illustrates the operations performed by the data processor of FIG. 1 to measure carbon concentration, according to the present invention.

Referring now to FIG. 2, the operations performed by the processor 13 of FIG. 1 Will now be described. Processor 13 obtains the gray scale values for the sensed area, either directly, or by digitizing the camera video signal, as shown at block 21. The control of black and white camera 12 by processor 13 is well known to those having skill in the art and need not be described in further detail. Once a 512×512×8 bit digital image array is obtained, all of the eight bit gray scale values for all 512×512 points are summed at block 22. Then, the summed value is divided by the number of values, i.e. 512×512, at block 23.

Then, at block 24, the optical density is calculated, by applying the following mathematical relationship:

$$OD = -10\ LOG_{10}(AGV_{Sample}/AGV_{Ref}) \qquad (1)$$

where $AGV_{Sample}$ is the average gray scale value of the carbon-containing sheet and $AGV_{Ref}$ is the average gray scale of a sheet with 0% carbon.

It will be understood by those having skill in the art that the reference value (for a carbon-free sheet) may be preset in the processor 13, based upon previously measured or calculated values. Alternatively, apparatus 10 may measure a carbon-free sheet prior to or after measuring the carbon-containing sheet, to obtain a reference value.

In a preferred embodiment of the invention, each carbon-containing sheet includes a carbon-free portion, at a predetermined location thereon, so that a reference value for each sheet may be obtained for use in determining optical density for that sheet. When each sheet includes a carbon-free portion, data processor 13 may control conveyor 16 to obtain an optical density measurement for the carbon-free portion and one or more optical density measurements for the carbon-containing portion of the sheet. The carbon-free optical density measurement may be obtained prior to or after the carbon-containing optical density measurement.

As indicated previously, the present invention may be employed to measure concentration of any material in any sample as long as the material blocks or reflects visible radiation incident upon the sample. In other words, any sample that visibly changes in opacity as a function of concentration of the material therein may be measured according to the present invention. For example, the concentration of materials such as coloring agents or dyes in samples of cigarette paper or filter paper may be measured. Food preparation applications include measurements of the amount of cooking based upon a measure of food color. For example, baking may be measured by measuring "brownness" Dye and paint color concentration may also be measured The sample need not be in the form of a thin sheet because optical intensity may be measured in a transmission or reflection mode.

As can be seen from the above discussion, the method and apparatus of the present invention provides simplified concentration measurement. Measurement is provided nondestructively at high speed and may be highly automated. Readily available components may be integrated to form the apparatus. These advantages contrast sharply with known chemical procedures which are slow, destructive and require specialized chemical equipment and chemicals.

In order to validate the method and apparatus of the present invention compared to conventional vapor absorption and wet digestion procedures, the correlation between the two methods was obtained, as described below. In a first Example eight carbon-containing filter sheets having carbon concentration in the 10.2–31.4% range were found to have a correlation of 0.99 and a standard error of calibration of ±1.0%. In a second Example, eight carbon-containing sheets having carbon concentration in the 9.4–28.1% range were found to have a correlation of 0.98 and a standard error of performance of ±1.4%. These results indicate that highly accurate measurements were obtained. The two Examples are described below.

EXAMPLE 1

For this Example, the system 10 of FIG. 1, including a Sony DXC-M2 camera 12 and an IBAS image processing system 13, was employed with a diffused lighting source 15 using fluorescent room light and a four inch ring light with full annular output. The ring light was attached to an Introlux Model 100 light module with a 12 volt, 100 watt tungsten lamp via a three foot fiber optic bundle. The light module, fiber bundle and ring light were manufactured by Volpi AG, Zurich, Switzerland. The dimensions of the carbon-containing filter sheets were approximately 8.5"×11". The camera 12 was adjusted to focus on a 3"×3" section of the sheet.

The dynamic range of the system was set by adjusting the tube voltage and the f/stop on the lens for both the lowest (blank-0%) and the highest (31.4%) carbon content samples, in order to obtain the highest sensitivity without saturating the sensor (the "blooming" effect) with the most reflective sample. Accordingly, the system was then calibrated to read an average gray scale value of 216.14 for the blank sample. The program contained in the IBAS processor acquired the image from the camera, and digitized the image and computed the average gray scale value and a standard deviation of the captured image.

Five images of 3"×3" sections of each sample sheet were acquired, and the average gray scale value and standard deviation of each image was calculated and saved for analysis. The data acquisition and computation time for each image was less than five seconds. The optical density value was computed for all of the samples using Equation (1). A simple least-squares linear regression procedure was used to develop a linear model of carbon versus optical density. The computed linear equation was $$\% \ Carbon = 0.52 \pm 2.57 \ (OD) \tag{2}$$

This equation had a high correlation coefficient of 0.99 with chemical concentration measuring techniques. Table I shows the data and statistics for the eight samples of Example I:

TABLE I

| Sample No. | OD | Chemical (%) | Optical (%) | Difference (%) |
|---|---|---|---|---|
| 1 | 11.54 | 31.4 | 30.1 | 1.3 |
| 2 | 11.52 | 29.3 | 30.1 | −0.8 |
| 3 | 7.89 | 22.1 | 20.8 | 1.3 |
| 4 | 7.81 | 18.8 | 20.6 | −1.8 |
| 5 | 7.55 | 19.7 | 19.9 | −0.2 |
| 6 | 6.73 | 17.3 | 17.8 | −0.4 |
| 7 | 4.35 | 11.9 | 11.7 | 0.2 |
| 8 | 3.62 | 10.2 | 9.8 | 0.4 |
|  |  | Avg. = 20.1% | Avg. = 20.1% | S.E.C. = ±1.0% |

For each sample, Table 1 indicates the percent carbon concentration using optical density according to the present invention ("Optical") and the percent carbon using the known chemical wet digestion technique ("Chemical"). The difference is also shown. It will be seen in an average of 20.1% carbon was obtained for both chemical and optical results, with a standard error of calibration (S.E.C.) of ±1.0%.

Figure 3:
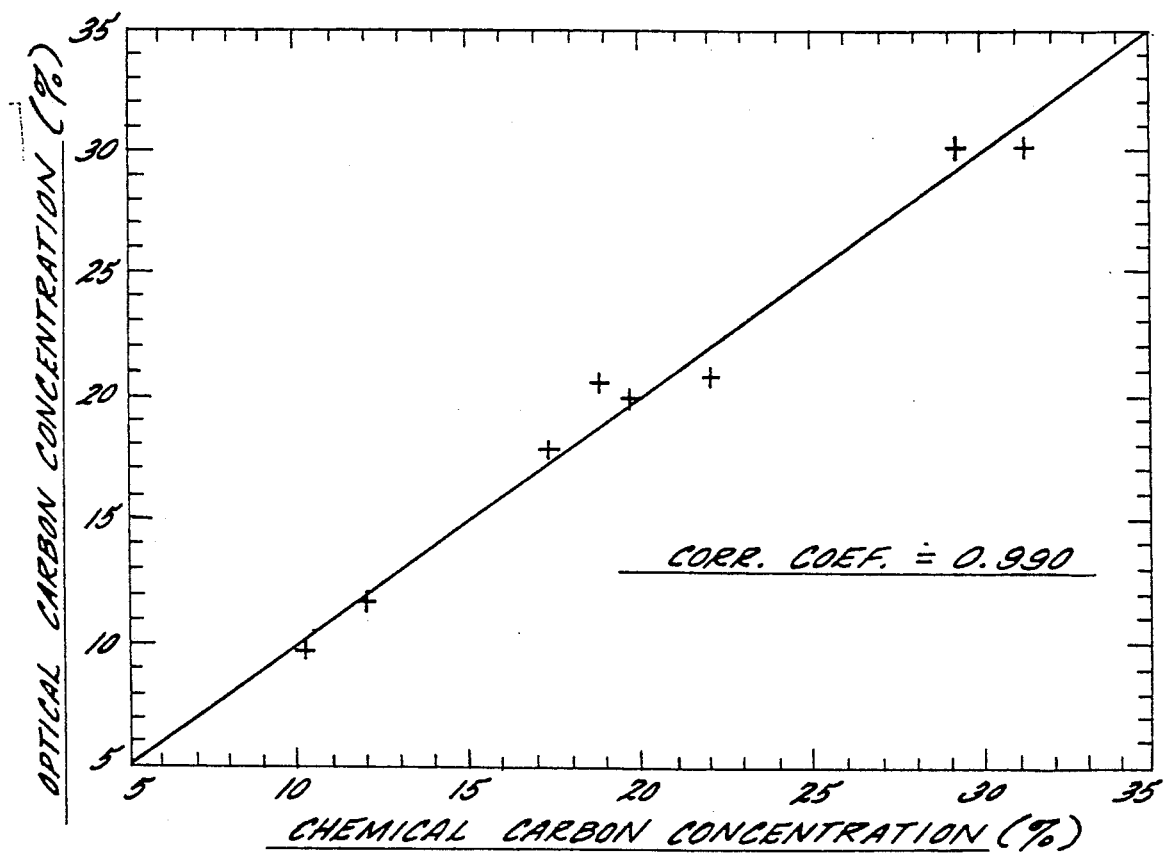
FIGS. 3-4 graphically illustrate the high correlation between the optical carbon concentration measurement according to the present invention, and chemically measured carbon concentration.

FIG. 3 illustrates a plot of chemical carbon concentration versus optical carbon concentration. A high correlation coefficient and a low standard error of calibration (S.E.C.) is shown.

EXAMPLE 2

The same test was performed on a second set of eight samples. The data and statistics are shown in Table II.

TABLE II

| Sample No. | OD | Chemical (%) | Optical (%) | Difference (%) |
|---|---|---|---|---|
| 1 | 10.94 | 28.1 | 28.6 | −0.5 |
| 2 | 7.24 | 20.3 | 19.1 | 1.2 |
| 3 | 7.40 | 19.0 | 19.5 | −0.5 |
| 4 | 6.71 | 17.9 | 17.7 | 0.2 |
| 5 | 6.23 | 15.7 | 16.5 | −0.8 |
| 6 | 6.56 | 15.0 | 17.4 | −2.4 |
| 7 | 3.30 | 11.0 | 9.0 | 2.0 |
| 8 | 3.09 | 9.4 | 8.4 | 1.0 |
|  |  | Mean = 17.1 | Mean = 17.0 | S.E.P. = ±1.4% |

Figure 4:
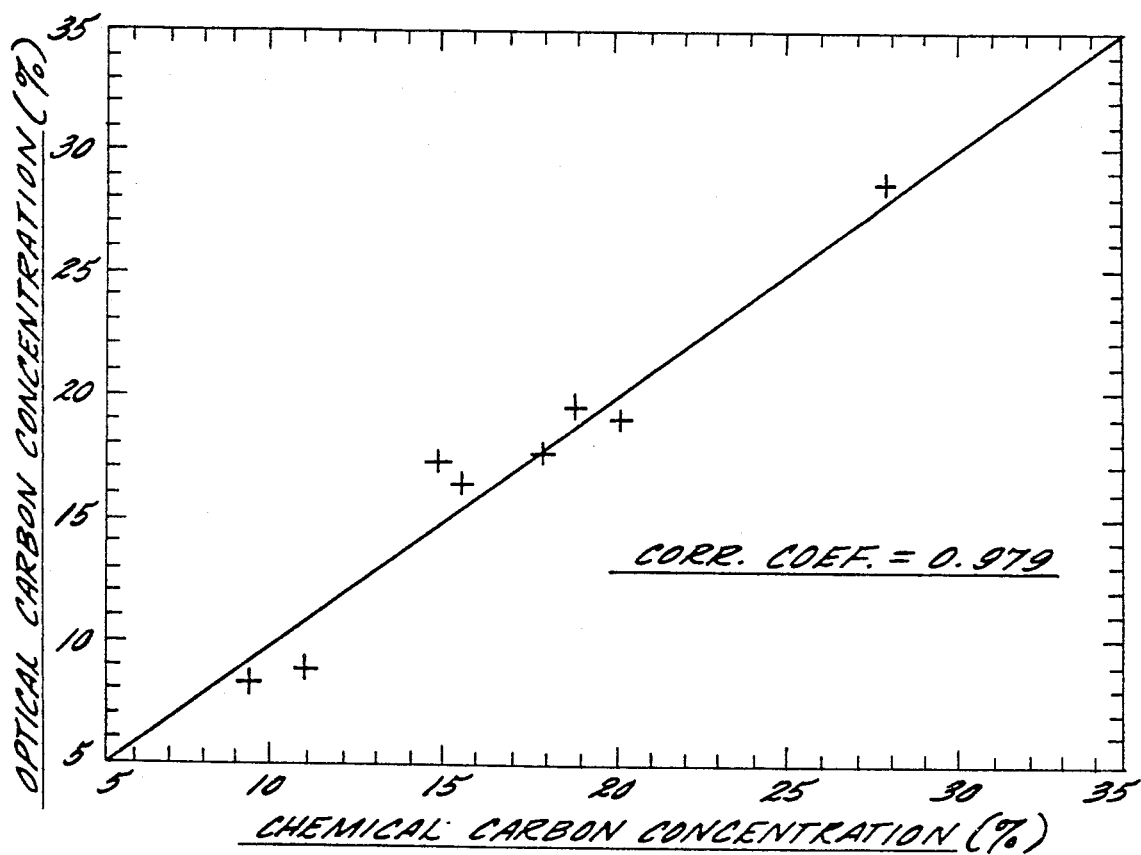

The correlation for this data set was also close to unity, i.e. 0.98. The S.E.P. was slightly higher at ±1.4%. FIG. 4 shows the plot of optical carbon concentration and chemical carbon concentration for Example 2.

During the performance of the experiments, it was observed that wrinkles in the sheet caused some inconsistent readings due to specular reflection. Specular reflection may be reduced by better care and handling of the sheets. Also, an integrated sphere and/or polarizers may be used to eliminate specular reflection. Thus, it is reasonable to assume that the absolute error of the measurement system may be even smaller than ±1.4% if these steps are taken.

The results shown for Examples 1 and 2 verify the accuracy of the method and apparatus of the present invention. The technique is fast, nondestructive as well as accurate to within a desired measurement error.

In the drawings and specification, there have been disclosed typical preferred embodiments of the invention and, although specific terms are employed, they are used in a generic and descriptive sense only and not for purposes of limitation, the scope of the invention being set forth in the following claims.

That which I claims is:

1. A method for measuring carbon concentration in a carbon-containing sample, comprising the steps of:
    optically sensing a two-dimensional portion of the carbon-containing sample;
    converting the optically sensed two-dimensional portion of the carbon-containing sample into a first two-dimensional digital image having a first two dimensional array of points, each having a digital value related to the sensed optical intensity thereat;
    obtaining a first average digital value for the first two-dimensional array of points;
    optically sensing a two-dimensional portion of a sample which is free of carbon;
    converting the optically sensed two-dimensional portion of the carbon-free sample into a second two-dimensional digital image having a second two-dimensional array of points, each having a digital value related to the sensed optical intensity thereat;
    obtaining a second average digital value for the second two-dimensional array of points; and
    comparing the first and second average digital values to nondestructively and accurately measure carbon concentration in said carbon-containing sample.

2. The method of claim 1 wherein the steps of optically sensing a two-dimensional portion of the carbon-containing sample and optically sensing a two-dimensional portion of the carbon-free sample comprise the steps of impinging optical radiation on the two-dimensional portion of said carbon-containing sample and said carbon-free sample, respectively, and sensing the optical radiation reflected from the two-dimensional portion of said carbon-containing sample and said carbon-free sample, respectively.

3. The method of claim 1 wherein the steps of optically sensing a two-dimensional portion of the carbon-containing sample and optically sensing a two-dimensional portion of the carbon-free sample comprise the steps of impinging optical radiation on the two-dimensional portion of said carbon-containing sample and said carbon-free sample, respectively, and sensing the optical radiation transmitted through from the two-dimensional portion of said carbon-containing sample and said carbon-free sample, respectively.

4. The method of claim 1 wherein the steps of converting the optically sensed two-dimensional portion of the carbon-containing sample and converting the optically sensed two-dimensional portion of the carbon-free sample comprise the steps of converting the optically sensed two-dimensional portions into two-dimensional gray scale images, having first and second two-dimensional arrays of points, respectively, each having a digital gray scale value related to the sensed optical density thereat; and wherein the steps of obtaining a first and second average digital value comprise the steps of obtaining a first and second average digital gray scale value, respectively.

5. The method of claim 1 wherein said comparing step comprises the steps of:
    obtaining a ratio of the first and second average digital values; and
    obtaining the logarithm of the ratio, to thereby obtain a carbon concentration measurement.

6. The method of claim 1 wherein the first optically sensing, first converting and first obtaining steps are repeatedly performed upon selected two-dimensional portions of the carbon-containing sample.

7. The method of claim 1 wherein the carbon-containing sample comprises a carbon-containing sheet.

8. The method of claim 7 wherein said carbon-containing sheet comprises a cigarette plug.

9. The method of claim 7 wherein said carbon-containing sheet comprises a cigarette filter.

10. The method of claim 7 wherein said carbon-containing sheet comprises a carbon and tobacco containing flavor carrier sheet.

11. A method for measuring carbon concentration in two-dimensional portion of a carbon-containing sample comprising the steps of:
    obtaining an average gray scale optical intensity of said two-dimensional portion; and
    comparing the obtained average gray scale optical intensity and an average gray scale optical intensity of a reference, to thereby nondestructively and accurately measure carbon concentration in said two-dimensional portion.

12. The method of claim 11 wherein said comparing step comprises the steps of:
    obtaining a ratio of the obtained average gray scale optical intensity and the average gray scale optical intensity of the reference; and
    obtaining the logarithm of the ratio.

13. The method of claim 11 wherein said obtaining step is repeatedly performed upon selected two-dimensional portions of said carbon-containing sample.

14. The method of claim 11 wherein said carbon-containing sample comprises a carbon-containing sheet.

15. The method of claim 14 wherein said carbon-containing sheet comprises a carbon and tobacco containing flavor carrier sheet.

16. The method of claim 11 wherein said reference is a carbon-free sample.

17. A method for measuring concentration of a material contained in a sample, comprising the steps of:
    obtaining an average gray scale optical intensity of said sample; and
    comparing the obtained average gray scale optical intensity and an average gray scale optical intensity of a reference, to nondestructively and accurately measure concentration of the material contained in the sample.

18. The method of claim 17 wherein said comparing step comprises the steps of:
    obtaining a ratio of the obtained average gray scale optical intensity and the average gray scale optical intensity of the reference; and
    obtaining the logarithm of the ratio.

19. The method of claim 17 wherein said reference is a material-free sample.

20. A system for measuring carbon concentration in a carbon-containing sample, comprising:
    means for optically sensing a two-dimensional portion of the carbon-containing sample;
    means, connected to said optically sensing means, for converting the sensed two-dimensional portion of the carbon-containing sample into a two-dimensional digital image having a two-dimensional array of points, each having a digital value related to the sensed optical intensity thereat;

means, connected to said converting means, for obtaining an average digital value for the two-dimensional array of points; and means, connected to said obtaining means, for comparing the obtained average digital value with a reference digital value to thereby nondestructively and accurately measure carbon concentration of said carbon-containing sample 21. The system of claim 20 wherein said optically sensing means comprises means for impinging optical radiation on the two-dimensional portion of said carbon-containing sample, and for sensing optical radiation reflected therefrom.

22. The system of claim 20 wherein said optically sensing means comprises means for impinging optical radiation on the two-dimensional portion of said carbon-containing sample, and for sensing optical radiation transmitted therethrough.

23. The system of claim 20 wherein said converting means comprises means for converting the sensed two-dimensional portion of the carbon-containing sample into a two-dimensional digital gray scale image of points, each having a digital gray scale value related to the sensed optical density thereat.

24. The system of claim 20 wherein said reference digital value comprises the average optical intensity value of a carbon-free sample.

25. The system of claim 23 wherein said reference digital value comprises the average digital gray scale intensity value of a carbon-free sample.

26. The system of claim 20 wherein said means for comparing comprises means for obtaining the logarithm of the ratio of the obtained average digital value and the reference digital value.

27. The system of claim 20 wherein said carbon-containing sample comprises a carbon-containing sheet.

28. The system of claim 27 wherein said carbon-containing sheet comprises a cigarette plug.

29. The system of claim 27 wherein said carbon-containing sheet comprises a cigarette filter.

30. The system of claim 22 wherein said carbon-containing sheet comprises a carbon and tobacco containing flavor carrier sheet.

31. The system of claim 20 further comprising means for moving said carbon-containing sample relative to said optical sensing means to thereby optically sense a plurality of two-dimensional portions in the carbon-containing sample.

32. A system for measuring carbon concentration in a two-dimensional portion of a carbon-containing sample, comprising:

means for obtaining an average gray scale optical intensity of said two-dimensional portion; and means, connected to said obtaining means, for comparing the obtained average gray scale optical intensity and the average gray scale optical intensity of a reference, to thereby nondestructively and accurately measure carbon concentration in said two-dimensional portion.

33. The system of claim 32 wherein said reference comprises a carbon-free sample.

34. The system of claim 32 wherein said means for comparing comprises means for obtaining the logarithm of the ratio of the obtained average gray scale optical intensity and the average gray scale optical intensity of the reference.

35. The system of claim 32 wherein said carbon-containing sample comprises a carbon-containing sheet.

36. The system of claim 35 wherein said carbon-containing sheet comprises a carbon and tobacco containing flavor carrier sheet.

37. A system for measuring concentration of a material contained in a sample, comprising:

means for obtaining an average gray scale optical intensity of said sample; and means, connected to said obtaining means, for comparing the obtained average gray scale optical intensity and an average gray scale optical intensity of a reference, to thereby nondestructively and accurately measure concentration of the material contained in the sample.

38. The system of claim 37 wherein said means for comparing comprises means for obtaining the logarithm of the ratio of the obtained average gray scale optical intensity and the average gray scale optical intensity of the reference.

39. The system of claim 37 wherein said reference comprises a material-free sample.

40. A carbon sheet adapted for carbon concentration measurement comprising: a single sheet substrate, at least a first portion of said single sheet substrate containing carbon and at least a second portion of said single sheet substrate being carbon-free, whereby carbon concentration measurement of said first portion may be calibrated using said second portion.

41. The carbon sheet of claim 40 wherein said substrate comprises a single tobacco containing sheet.

42. The carbon sheet of claim 40 wherein said second portion is located in a predetermined area of said substrate.

43. The carbon sheet of claim 40 wherein said substrate includes menthol and glycerine applied thereon.

44. The carbon sheet of claim 40 wherein said carbon sheet comprises a carbon and tobacco containing flavor carrier sheet.

* * * * *